United States Patent [19]

Grendahl

[11] Patent Number: 4,764,169
[45] Date of Patent: Aug. 16, 1988

[54] INTRAOCULAR LENS

[76] Inventor: Dennis T. Grendahl, Excelsior Bay Gables, Excelsior, Minn. 55331

[21] Appl. No.: 938,071

[22] Filed: Dec. 4, 1986

[51] Int. Cl.$^4$ .............................................. A61F 2/16
[52] U.S. Cl. ...................................................... 623/6
[58] Field of Search ........................................... 623/6

[56] References Cited

U.S. PATENT DOCUMENTS

| | | |
|---|---|---|
| 4,159,546 | 7/1979 | Shearing ................................ 623/6 |
| 4,439,873 | 4/1984 | Poler ...................................... 623/6 |
| 4,562,600 | 1/1986 | Ginsberg et al. ...................... 623/6 |
| 4,605,409 | 8/1986 | Kelman ................................. 623/6 |
| 4,657,546 | 4/1987 | Shearing ................................ 623/6 |

FOREIGN PATENT DOCUMENTS 2124500A 2/1984 United Kingdom .................... 623/6

OTHER PUBLICATIONS

Lens Styles from Cilco (Advertisement Brochure) Cilco, Inc. 6 pages, style SK-4 on page 4 relied upon, Oct. 1982, pp. 1, 4 and 6 cited.

Primary Examiner—Ronald L. Frinks
Attorney, Agent, or Firm—Hugh D. Jaeger

[57] ABSTRACT

A light weight intraocular lens for placement in a capsular bag, including a small hard inner lens optic and a soft pliable skirt surrounding the lens optic. The lens optic is a bi-convex optic. The lens optic is a high refractive index material and has a diameter of about 2-4 mm and utilizes a laser discission yag space. The soft pliable skirt with an inner circumference channel secures about an edge of the lens optic and extends away at a downwardly sloping angle. The bottom edge of the skirt can be continuous or intermittent, and can include a single or dual ridge barrier. The outer diameter of the lens skirt can be up to 8-9 mm.

6 Claims, 3 Drawing Sheets

INTRAOCULAR LENS

BACKGROUND OF THE INVENTION

1. Field of the Invention

The present invention pertains to an intraocular lens, and more particularly, pertains to an intraocular lens, with a hard optic and channeled soft skirt, where the skirt is foldable allowing for insertion of the lens through a small incision in the eye.

2. Description of the Prior Art

The prior art has not demonstrated the aspects of a foldable lens including a hard optic. The foldable lenses of the prior art has usually been all silicone or other soft pliable material, which sometimes provides for distortion at the optical zone about the center of the lens.

The present invention overcomes the disadvantages of the prior art by providing a lighter weight foldable yag space lens with a hard optic of high refractive index material secured within an annular channel of a soft pliable skirt.

SUMMARY OF THE INVENTION

The general purpose of the present invention is to provide an intraocular lens which is intended for placement in the capsular bag, and allows for insertion of the lens through a small incision in the eye. The yag space lens is self centering and does not require any additional supporting structures. The lens optic can is bi-convex. The channeled skirt of the lens can include an appropriate single or double barrier ridge about the edge of the soft skirt.

According to one embodiment of the present invention, there is provided a lighter weight intraocular laser yag space lens for placement in a capsular bag, including a small hard high refractive inner lens optic and a grooved soft pliable outer skirt surrounding the lens optic. The lens optic material can be high refractive such as PMMA, polysulfonce, polycarbonate, or like biocompatible material. The lens diameter is about 2-4 mm. The channeled soft pliable skirt can be silicone, hydrogel, or a like material which is bicompatible, and contains an annular channel for engagement about the edge of the lens optic. The diameter is about 8-9 mm. The skirt assumes a convex - concave cross-section and can include an edge as well as a continuous or intermittent downwardly extending ridge, and a single or dual barrier ridge, or the like to take up slack in the capsular bag.

Significant aspects and features of the present invention include a bi-convex yag space lens which does not require any supporting structure and centers within the capsular bag.

Another significant aspect and feature of the present invention is a lens skirt which is foldable, allowing for insertion through a small incision in the eye, such as with a phaeko operation.

Another significant aspect and feature of the present invention is a lens optic fitting within an interior circumference annular groove in the pliable skirt.

Having thus described embodiments of the present invention, it is the principle object hereof to provide a yag space bi-convex intraocular lens with a hard high refractive non-foldable plastic center optic and a soft internally grooved foldable skirt surrounding the lens optic.

One object of the present invention is a lens which is self-centering within the capsular bag, and does not have any external mounted supporting structure.

Another object of the present invention is a channeled skirt for accepting an edge of a bi-convex lens.

BRIEF DESCRIPTION OF THE DRAWINGS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
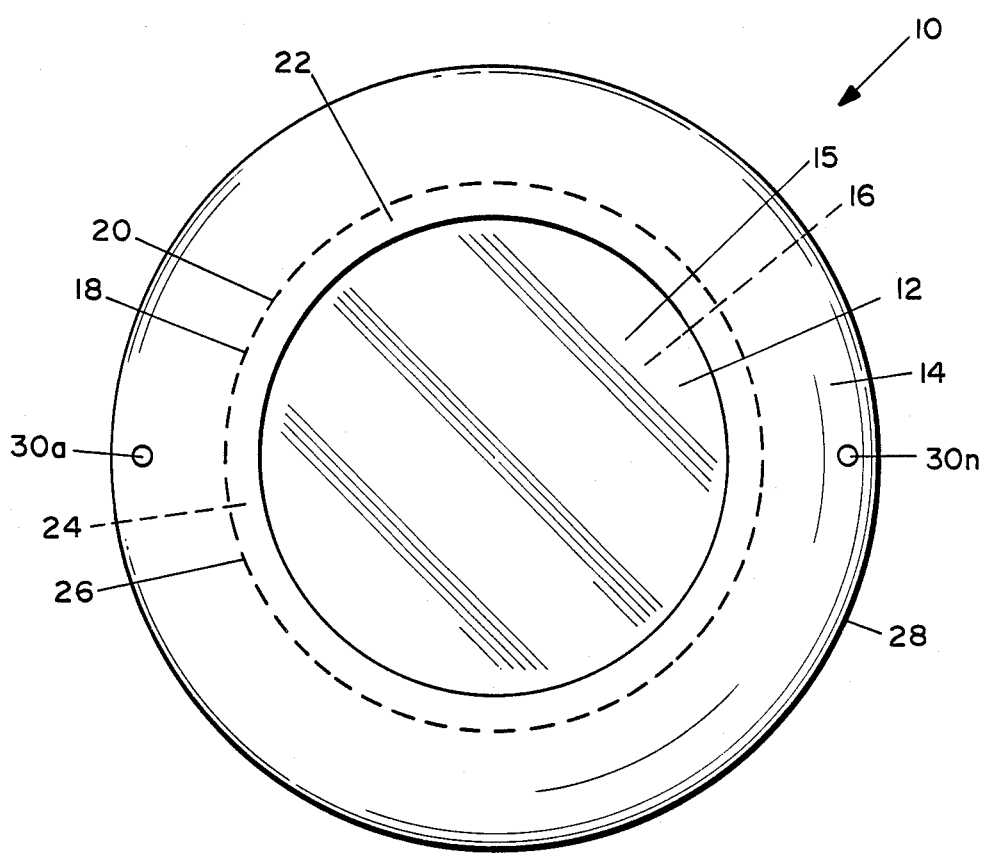
FIG. 1 illustrates a top view of an intraocular lens, the present invention.

FIG. 1 illustrates a top view of a light weight intraocular yag space lens 10, the present invention, including a hard optic 12, and a soft skirt 14. The hard optic 12 is of a high refractive index material such as PMMA, polysulfone, polycarbonate, or the like, and is of a diameter of 2-4 mm. The lens optic can assumes a bi-convex optic configuration. A bi-convex lens optic 12 has been illustrated in FIG. 1. Other lens configurations can include meniscus, plano-convex, or a reverse optic. The optic 12 of FIG. 1 includes an upper convex surface 14, a lower convex surface 16, and an edge 18. The soft skirt 14, is of a curved convex-concave rim cross-section configuration. The skirt 14 includes a configured annular channel or groove 20 including channel lips 22 and 24 and a channel bottom 26 in the inner circumference of the skirt 14. The optic edge 18 of optic 12 engages between the annular lips 22 and 24 and the annular channel bottom 26 of annular channel 20 thus positively securing the soft skirt 14 about the lens optic 12. The thickness of the skirt can be 0.05 to 0.5 mm. The edge of the skirt 28 is slightly rounded. The channeled skirt can be made of silicone, hydrogel, or other like biocompatible material. The outer diameter is 6-9 mm. The skirt can also be provided with positioning holes 30a-30n about the outer circumference of the skirt 14 as so desired.

Figure 2:
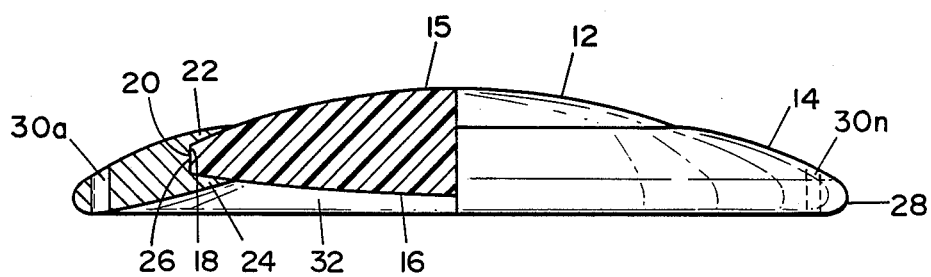
FIG. 2 illustrates a side view in partial cross section of FIG. 1.

FIG. 2 illustrates a side view in partial cross section of the intraocular lens 10, where all numerals correspond to those elements previously described. Particularly noted is the laser yag discission space 32 in the area immediately below the convex surface 16 of the hard optic 12 and above the plane of the bottom of the soft skirt 14.

Figure 3:
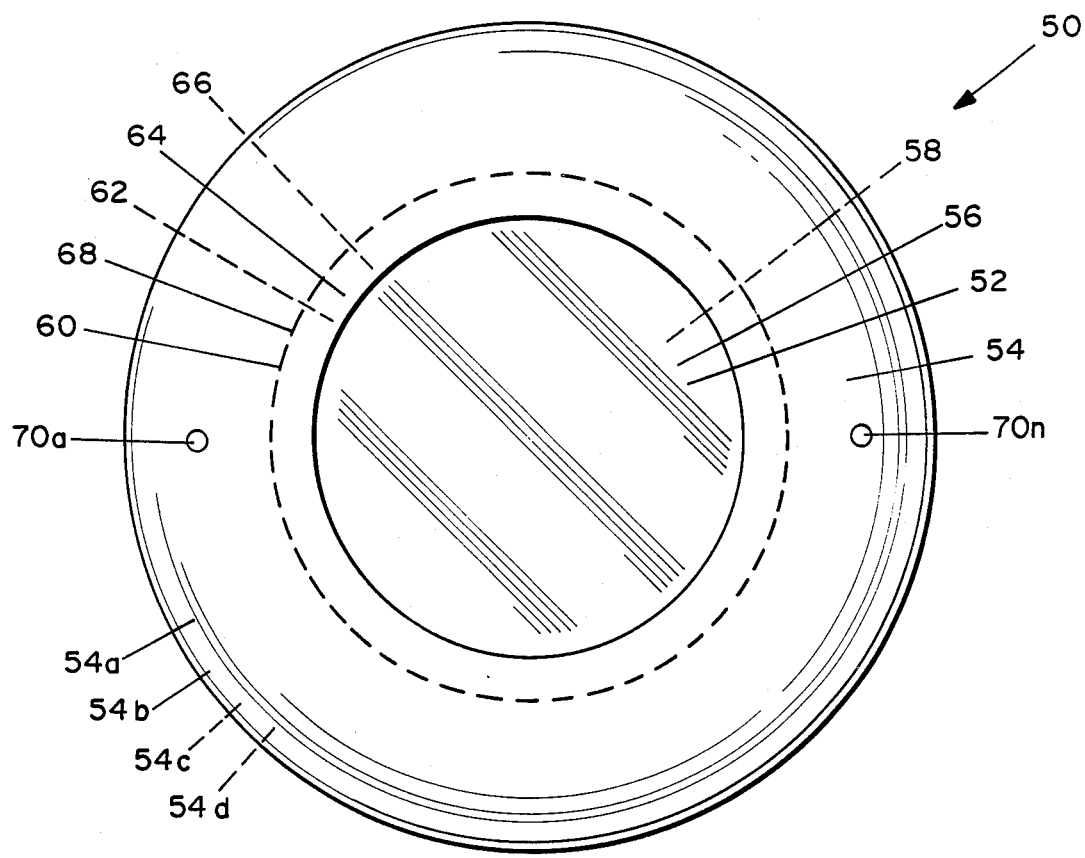
FIG. 3 illustrates an alternative embodiment of an intraocular lens including a barrier edge.

FIG. 3 illustrates a top view of an intraocular lens 50, the first alternate embodiment of the present invention, including a hard optic 52 and an angulated soft skirt 54 including a barrier ridge as later described in detail. The hard optic 52 is of a high refractive index material such as PMMA, polysulfone, polycarbonate, or the like, and is of a diameter of 2-4 mm as previously discussed. The lens optic can assume a bi-convex optic configuration. A bi-convex lens optic 52 is illustrated in FIG. 3. The optic 52 of FIG. 3 includes an upper convex surface 56, a lower convex surface 58, and an edge 60. The angulated soft skirt 54 is of a curved convex - concave rim cross-section configuration, and contains a configured channel or groove 62 including channel lips 64 and 66, and a channel bottom 68 in the inner circumference of the skirt 54. The optic edge 60 of optic 52 engages between annular lips 64 and 66, and against the channel bottom 68 of annular channel 62 thus positively securing the soft skirt 54 about the lens optic 52. Soft skirt 54 angles downwardly from 54a to form an angulated skirt edge 56b including a ridge barrier 54c, and including rounded edge 54d thus increasing yag space 70 as formed between the convex surface 58 and the plane of the bottom portion of rounded edge 54d to take up slack in the capsular bag. The ridge barrier can be either continuous or intermittent spacing. The thickness of the angulated skirt can be 0.05 to 0.5 mm. The channeled skirt can be made of silicone, hydrogel, or other like biocompatible material, the outer diameter is 6-9 mm. The skirt can also be provided with positioning holes 70a-70n about the outer circumference of the skirt 54 as so desired.

Figure 4:
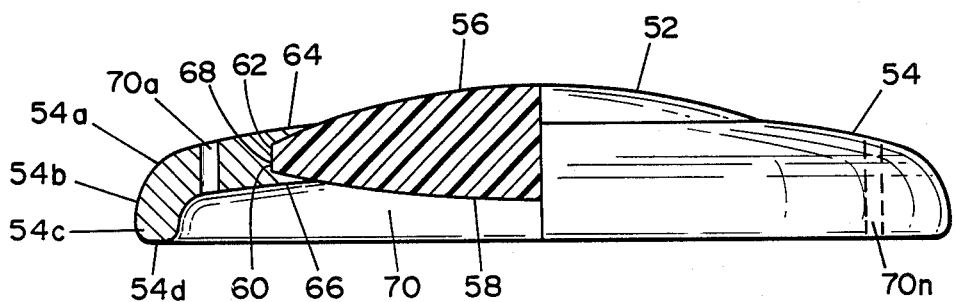
FIG. 4 illustrates a side view in partial cross section of FIG. 3.

FIG. 4 illustrates a side view of the intraocular lens 50, where all numerals correspond to those elements previously described. Particularly noted is the laser yag discission space 70 which has been increased essentially by the angulated skirt edge 54b to take slack out of the capsular bag.

Figure 5:
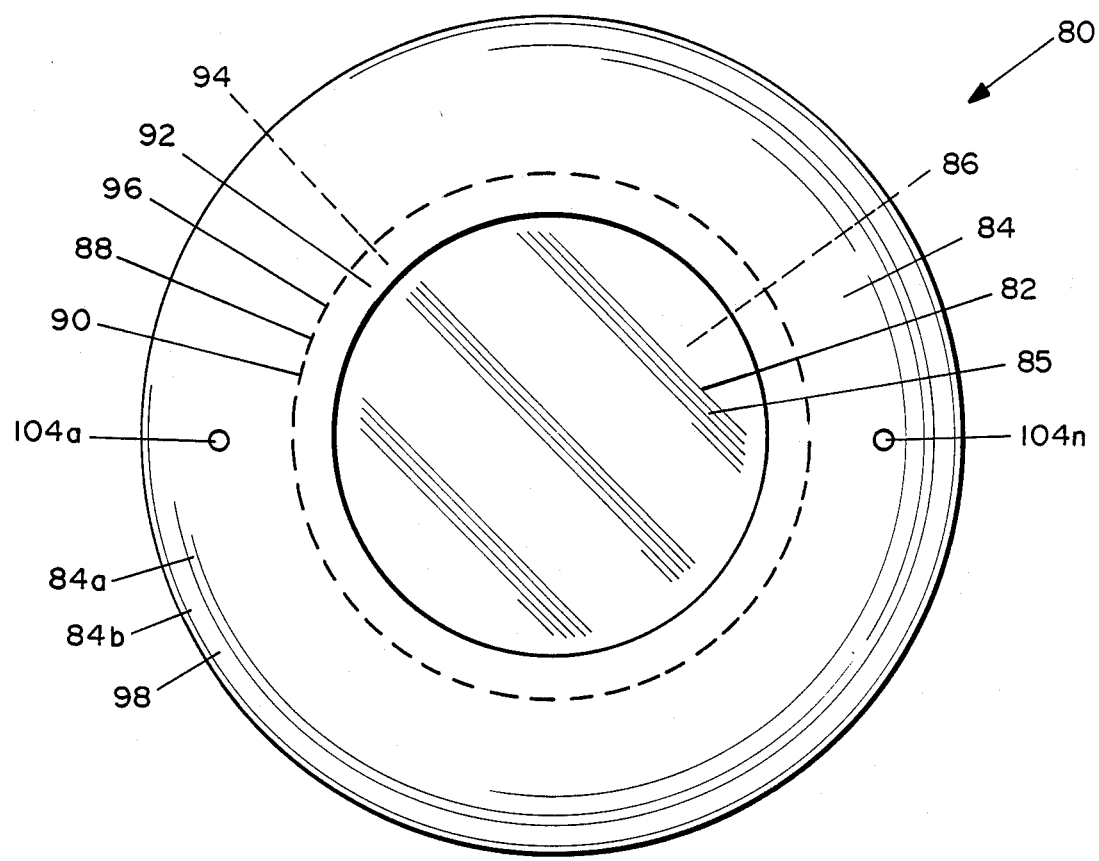
FIG. 5 illustrates an alternative embodiment of an intraocular lens including a dual barrier ridge; and, FIG. 6 illustrates a side view in partial cross section of FIG. 5.

FIG. 5 illustrates a top view of an alternate embodiment of an intraocular lens 80, the present invention, including a hard optic 82, and an angulated soft skirt 84 including a dual ridge barrier as later described in detail. The hard optic 82 is of a high refractive index material such as PMMA, polysulfone, polycarbonate, or the like, and is of a diameter of 2-4 mm. The lens optic can assume a bi-convex optic configuration. A bi-convex lens optic 82 has been illustrated in FIG. 5. The optic 82 of FIG. 5 includes an upper convex surface 85, a lower convex surface 86, and an edge 88. The soft skirt 84 is of a curved convex - concave rim cross-section configuration and contains a configured channel or groove 90 including channel lips 92 and 94, and a channel bottom 96 in the inner circumference of the skirt 84. The optic edge 88 of optic 82 engages between annular lips 92 and 94 and against the channel bottom 96 positively securing the soft skirt 84 about the lens optic 82. The soft skirt angles downwardly from 84a to form an angulated skirt edge 84b including a dual ridge barrier 98 including rounded concentric barrier elements 98a and 98b with a separating channel 100 between them. The yag space 102 is formed between the convex surface 86 and the plane of the bottoms of the barrier elements 98a and 98b to take up slack in the capsular bag. The dual ridge barrier can use either continuous or intermittent spacing. The thickness of the angulated skirt can be 0.05 to 0.5 mm. The skirt can be made of silicone, hydrogel, or other like biocompatible material and would have an outer diameter of 8-9 mm. The skirt can also be provided with positioning holes 104a-104n about the outer circumference of the skirt 54 as so desired.

Figure 6:
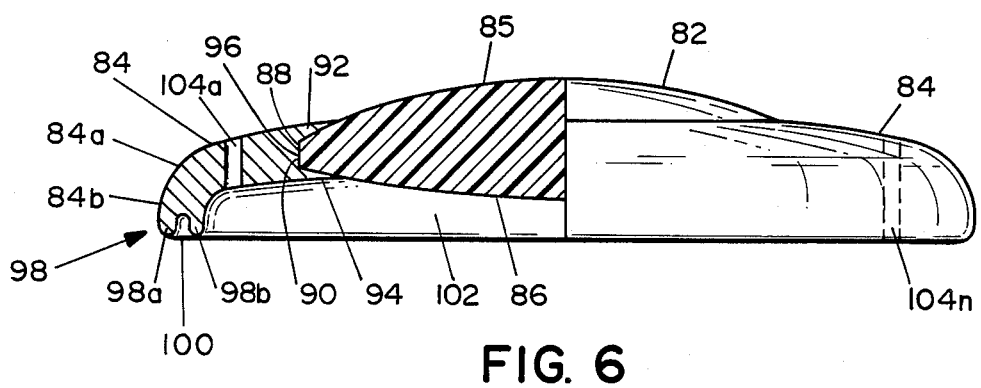

FIG. 6 illustrates a side view of the intraocular lens 80, where all numerals correspond to those elements previously described. Particularly noted is the laser yag discission space 102 which has been increased essentially by the angulated skirt edge 84b to take slack out of the capsular bag.

MODE OF OPERATION

The lenses of FIGS. 1-6 provide that the skirt can be folded about the hard lens optic allowing for insertion of the lens in a small incision in the eye similar to that of a phaeko operation. The hard optic, of course, is nonfoldable, but the skirt is soft enough to be pliable, and is secured in place about the hard optic by use of a groove. The soft skirt provides for placement in the capsular bag and is inherently self centering. The lens also has the advantage of having no loops which require subsequent placement.

Various modifications can be made to the present invention without departing from the apparent scope thereof.

I claim:
1. Intraocular lens, free of haptic loops, comprising:
   a. hard bi-convex lens optic of high refractive index material; and,
   b. channeled soft skirt surrounding the edge of said lens optic and of a foldable material, and angulated skirt edge means extending downwardly therefrom an upper surface of said skirt and forming a barrier ridge and forming two concentric rings which act as a dual barrier ridge.
2. Lens of claim 1, wherein said material of said lens optic is PMMA, polysulfone, polycarbonate, or like high refractive index material.
3. Lens of claim 1, wherein said soft skirt is of silicone, hydrogel or like foldable material.
4. Lens of claim 1, wherein said center optic is 2-4 mm. diameter.
5. Lens of claim 1, wherein said skirt has an outer diameter of 6-9 mm.
6. Lens of claim 1, wherein said skirt thickness is 0.05-0.5 mm.

* * * * *